United States Patent [19]
Safe

[11] Patent Number: 5,948,808
[45] Date of Patent: Sep. 7, 1999

[54] INDOLE-3-CARBINOL, DIINDOLYLMETHANE AND SUBSTITUTED ANALOGS AS ANTIESTROGENS

[75] Inventor: Stephen H. Safe, College Station, Tex.

[73] Assignee: The Texas A&M University System, College Station, Tex.

[21] Appl. No.: 08/813,365

[22] Filed: Mar. 7, 1997

[51] Int. Cl.$^6$ .................. A61K 31/40; A61K 31/405; C07D 209/04; C07D 309/12
[52] U.S. Cl. .................. 514/415; 514/414; 514/418; 548/455; 548/483; 548/484; 548/485; 548/486; 548/509
[58] Field of Search ..................... 514/414, 415, 514/418; 548/455, 483, 484, 485, 486, 509

[56] References Cited

PUBLICATIONS

Hanley et al., Indole Glucosinolates and Phytoalexins in Cruciferous Crops, pp. 44–46, 1990.
Krichevskii et al., Synthesis of Azoxyindole Derivatives, Chemistry of Heterocyclic Compounds, vol. 26, No. 5, pp. 622–624, May 1990.
Rannug et al., Use Of Artificial Intelligence In Structure–Affinity Correlations Of 2,3,7,8–Tetrachlorodibenzo–p–dioxin (TCDD) Receptor Ligand, Carcinogenesis, vol. 12, No. 11, pp. 2007–2015, Nov. 1991.
Jackson et al., Electrophilic Substitution In Indoles, J. Chem. Soc. Perkin Trans. 1, No. 11, pp. 2543–2551, Nov. 1987.
Bergman, Synthesis of Some 3–Indolylvinylene Ketones, Acta Chemica Scandinavica, vol. 26, No. 3, pp. 970–974, 1972.
Hill et al., Light–Induced Reactions of alpha–N–Alkylanilino–Ketones: Formation of Di–indolylmethanes, J.C.S. Perkin Trans 1, No. 9/10, pp. 1210–1219, 1972.
Lerch et al., Carbodiimide–Sulfoxide Reactions, J. Org. Chem., vol. 36, No. 25, pp. 3861–3869, Dec. 1971.
Bergman et al., Terpenoid N–heterocycles, Acta Chemica Scandinavica, vol. 23, No. 8, pp. 2578–2582, 1969.
Foldeak et al., CA64:9670c and CA64:9670d, 1966.
Noland et al., CA59:15247a, 1963.
Berti et al., CA55:14455h and CA55:14556e, 1960.
Leete, CA54:6684a, CA54:6684b, CA54:6684c and CA54:6684d, 1959.
Plikhtyak et al., 3–Hydroxymethylation of Indoles and Synthesis of Ascorbigens, Khim. Farm. Zh., vol. 25, No. 6, pp. 57–59, 1991.
Hanley et al., Chemistry Of Indole Glucosinolates: Intermediacy Of Indol–3–ylmethyl Isothiocyanates In The Enzymic Hydrolysis Of Indole Glucosinolates, J. Chem. Soc., Perkin Trans. 1, No. 8, pp. 2273–2276, Aug. 1990.
Dashwood et al., The Synthesis of [3H]–Indole–3–Carbinol, A Natural Anti–Carcinogen From Cruciferous Vegetables, Journal of Labelled Compounds and Radiopharmaceuticals, vol. 27, No. 8, pp. 901–907, Aug. 1989.

Bukin et al., Ascorbingen and Its Derivatives as Depot–Forms of Ascorbic Acid, Bioorganic Chemistry, vol. 13, No. 4, pp. 539–545, 1987.
Mukhanov et al., Ascorbigen and Its Derivatives, Bioorganic Chemistry, vol. 10, No. 4, pp. 544–559, 1984.
Francis et al., Mass Spectrometric and Chromatographic Characteristics of Neutral and Acidic 5–Methoxyindoles and Some Related Compounds, Biomedical Mass Spectrometry, vol. 7, No. 7, pp. 294–300, 1980.
Dmitrienko et al., The Bromination and Chlorination of 2,3–Dialkylindoles. Isolation of 3–Bromo– and 3–Chloro–2, 3–dialkylindolenines and Acid Catalyzed Conversion to 3–Methoxyindolenines, Canadian Journal of Chemistry, vol. 58, No. 8, pp. 808–814, 1980.
Mattocks, Pyrrolizidine Alkazloid Analogues, J.C.S. Perkin Trans. 1, No. 8, pp. 896–905, 1978.
Noland et al., Synthesis and Reactions of 5–Bromskatole and 5–Bromo–1,3–dimethylindole, Journal of Organic Chemistry, vol. 32, No. 3, pp. 828–832, 1967.
Beti et al., CA56:11541e, 1961.
El Gihani et al., Scandium And Cooper Triflate–Catalysed Acylaminoalkylation And Friedel–Crafts Alkylation Reactions, Synlett, No. 9, pp. 871–872, Sep. 1996.
Suda et al., A Novel Electrochemical Oxidation Reactions Utilizing Cyclodextrins. Anodic Oxidation of Indole–Cyclodextrin–Alcohol System, Chemistry Letters, No. 10, pp. 1915–1916, 1994.
Saceda, M., et al., "Regulation of the Estrogen Receptor in MCF–7 Cells by Estradiol", Mol. Endo. 1988, vol. 2, No. 12, pp. 1157–1162.
Guilbaud, N., et al., "Effects of Differentiation–Inducing Agents on Maturation of Human MCF–7 Breast Cancer Cells", Jour. Of Cell. Phys. 1990, vol. 145, No. 1, pp. 162–172.
Alexander, I., et al., "Progestin Regulation of Estrogen Receptor Messenger RNA in Human Breast Cancer Cells", Mol. Endo. 1990, vol. 4, No. 6, pp. 821–828.
Garcia–Morales, P. et al., "Effect of Cadmium on Estrogen Receptor Levels and Estrogen–induced Responses in Human Breast Cancer Cells*", Jour. of Bio. Chem. 1994, vol. 269, No. 24, pp. 16896–16901.
Liu, H., et al. "Indolo[3,2–b]carbazole: a Dietary–Derived Factor That Exhibits Both Antiestrogenic and Estrogenic Activity." J. Natl. Cancer Inst. 86(23):1758–1765, (1994).

*Primary Examiner*—Mukund J. Shah
*Assistant Examiner*—Brenda Coleman
*Attorney, Agent, or Firm*—Baker & Botts, LLP

[57] ABSTRACT

Provided in the present invention are compounds and compositions of substituted indole-3-carbinols and diindolylmethane suitable for treating estrogen-dependent tumors. Also provided are methods of treating such cancerous-conditions.

14 Claims, No Drawings

OTHER PUBLICATIONS

Chen, I., et al. "Inhibition of TCDD–Induced Responses in B6C3F1 Mice and Hepa 1c1c7 Cells by Indole–3–Carbinol." *Organohalogen Compounds* 25:57–60, (1995).

Chen, I., et al. Indole–3–carbinol and Diindolylmethane as Aryl Hydrocarbon (Ah) Receptor Agonists and Antagonists in T47D Human Breast Cancer Cells. *Biochem. Pharmacol.* 51:1069–1076, (1996).

Safe, S.H., et al. "Dietary Indoles with Antiestrogenic Activity in Common Vegetables and Their Implications." In: *Estrogens, Progestins and Their Antagonists* (E. Pavlik, ed.), Birkhouser, Boston. pp. 73–97, 1996.

Mukhanov et al., Neoascorbigen and Its Analogs: Synthesis and Study, Khim. Farm. Zh., vol. 28, No. 7, pp. 6–10, 1994.

Yamada et al., A Synthesis Method Of Indole–3–Methanamine And/Or Gramine From Indole–3–Carboxaldehyde, And Its Application For The Synthesis Of Brassinin, Its 4–Substituted Analogs, And 1,3,4,5–Tetrahydropyrrolo[4,3,2–de]quinoline, Heterocycles, vol. 36, Dec. 1993.

Harrison et al., Synthesis Of Cyclopent[b]indoles By Formal [3+2]–Addition Of Indolylmethyl Cations To Alkenes, Tetrahedron Letters, vol. 34, No. 52, pp. 8527–8530, 1993.

Toyota et al., Tandem Michael Addition–[3,3]Sigmatropic Rearrangement Processes. Part 2. Construction Of Cyclopropa[3,4]pyrrolo[3,2–e]indol–4–one (CPI) Unit Of Antitumor Antibiotic CC–1065, Chem. Soc. Perkin Trans. 1, No. 5, pp. 547–552, Mar. 1992.

INDOLE-3-CARBINOL, DIINDOLYLMETHANE AND SUBSTITUTED ANALOGS AS ANTIESTROGENS

BACKGROUND OF THE INVENTION

1. Field of the Invention

The present invention relates to substituted indole-3-carbinol and diindolylmethane compounds and pharmaceutical compositions. The present invention also relates to the use of substituted indole-3-carbinol and diindolylmethane compositions in treating estrogen dependent tumors.

2. Description of the Prior Art

Breast cancer is one of the leading causes of premature death in North American women, and the formation and growth of both breast and endometrial tumors are estrogen-dependant. Mammary cancer is a complex disease process in which treatment with antiestrogens (endocrine therapy) or antineoplastic drugs depends on a number of factor including levels of estrogen receptor (ER) expression. The development of rational treatment strategies for mammary cancer is dependent on understanding regulation of mammary cancer development and growth and inhibition of these responses.

There is considerable evidence showing that steroid hormones are involved in development of some tumors, and treatment of these tumors has utilized strategies that modulate endocrine response pathways. For example, estrogens play a role in development and growth of mammary tumors in human and animal models, and various antiestrogens are utilized as endocrine therapies for treatment of this disease (Lerner L. J., et al., Cancer Res. 50:4177–4189, 1990). Antiestrogens are a class of chemicals which inhibit estrogens from eliciting their full response in target tissues. They can be used to explore the mechanisms of action of estrogens and to provide treatment for estrogen-dependent diseases (e g., tumors). An antiestrogenic compound currently being utilized in the treatment of mammary cancer is tamoxifen. Progesterone and related progestins have also been used extensively to treat mammary cancer in laboratory animals and humans. Numerous other antiestrogens have been disclosed in recent years including inhibitors of aromatase (Bednarski U.S. Pat. No. 4,745,109), antiestrogenic hydrazones (Morgan U.S. Pat. No. 4,732,904) and antiestrogenic benzothiophenes (Jones U.S. Pat. No. 4,418,068). Several studies have indicated that diet can influence the process of carcinogenesis, and both fruit and vegetables are reported to possess antimutagenic and anticarcinogenic properties in human, animal and cell models (Aldercreutz, Envir. Health Persp. 103(57) 103–112,1995). Cruciferous vegetables including broccoli, cauliflower, Brussels sprouts, and cabbage contain several compounds such as indoles, isothiocyanates and dithiolthiones which modulate carcinogenesis in different animal models. For example, glucobrassicin (3-indolymethyl glucosinolate), a major component of cauliflower (0.1 to 1.6 mmol/kg), cabbage (0.1 to 1.9 mmol/kg), and Brussels sprouts (0.5 to 3.2 mmol/kg), is readily converted to indole 3-carbinol (I3C). I3C and related compounds inhibit formation or growth of estrogen-regulated tumors in the rodent mammary, endometrium and uterus, suggesting that this compound may be acting as an antiestrogen. Wattenberg and Loub (Wattenberg L. W., et al., Cancer Res. 38:1410–1413, 1978) first showed that oral administration of I3C and its dimerization product, 3,3'diindolylmethane (DIM), 20 hours prior to treatment with DMBA, inhibited the occurrence of mammary tumors in female Sprague-Dawley rats, and dietary administration of Brussels sprouts also provided some protective effects. Several studies have reported that I3C inhibits mammary carcinogenesis in rodent models, thus exhibiting antiestrogenic activity (Kojima T. et al, Cancer Res. 54:1446–1449, 1994; Grubbs C. J. et al, Anticancer Res. 15:709–716, 1995). Dietary I3C and 20% Brussels sprouts inhibited DMBA-induced mammary tumor formation and progression (Stoewsand G. S. et al, Cancer Lett. 39:199–207, 1988). A recent study evaluated the effects of I3C on both DMBA- and methylnitrosourea (MNU)-induced mammary tumors in female Sprague-Dawley rats using several different treatment protocols (Grubbs C. J. et al, Anticancer Res. 15:709–716, 1995). However, none of these investigations have shown the utility of substituted I3C and DIM as antiestrogenic agents.

These and other advantages of the present invention will become apparent from the following detailed description.

SUMMARY OF THE INVENTION

Provided herein is a compound

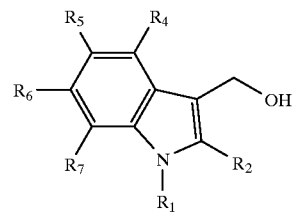

where $R_1$, $R_2$, $R_4$, $R_5$, $R_6$, and $R_7$ individually and independently, is a hydrogen, or a substituent selected from the group consisting of a halogen, a nitro group, and a linear or branched alkyl or alkoxy group of about one to about ten carbons, said compound having at least one substituent.

Also provided in the present invention is a compound selected from the group consisting of 5-methyl-indole-3-carbinol, 5-ethyl-indole-3-carbinol, 5-propyl-indole-3-carbinol, 5-butyl-indole-3-carbinol, 5-pentyl-indole-3-carbinol, 5-methoxy-indole-3-carbinol, 5-ethoxy-indole-3-carbinol, 5-propyloxy-indole-3-carbinol, 5-butyloxy-indole-3-carbinol, 5-amyloxy-indole-3-carbinol, N-methyl-indole-3-carbinol, N-ethyl-indole-3-carbinol, N-propyl-indole-3-carbinol, N-butyl-indole-3-carbinol, N-pentyl-indole-3-carbinol, 2-methyl-indole-3-carbinol, 2-ethyl-indole-3-carbinol, 2-propyl-indole-3-carbinol, 2-butyl-indole-3-carbinol and 2-pentyl-indole-3 -carbinol.

It is a further object of the present invention to provide a pharmaceutical composition comprising a biologically active amount of a compound

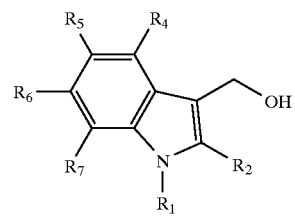

where $R_1$, $R_2$, $R_4$, $R_5$, $R_6$, and $R_7$, individually and independently, is a hydrogen, or a substituent selected from the group consisting of a halogen, a nitro group, and a linear or branched alkyl or alkoxy group of about one to about ten carbons, said compound having at least one substituent, and a pharmaceutically acceptable carrier.

It is also an object of the present invention to provide a method of treating estrogen-dependent tumors comprising administering a biologically active amount of a compound

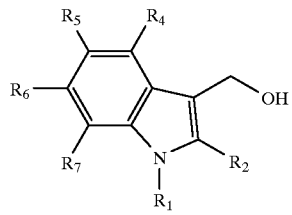

where $R_1$, $R_2$, $R_4$, $R_5$, $R_6$, and $R_7$, individually and independently, is a hydrogen, or a substituent selected from the group consisting of a halogen, a linear or branched alkyl or alkoxy group of about one to about ten carbons, and a nitro group said compound having at least one substituent.

Also provided in the present invention is a compound

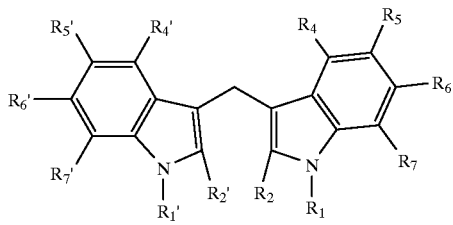

where $R_1$, $R_2$, $R_4$, $R_5$, $R_6$, $R_7$, $R_1'$, $R_2'$, $R_4'$, $R_5'$, $R_6'$, and $R_7'$, individually and independently, is a hydrogen, or a substituent selected from the group consisting of a halogen, a nitro group, and a linear or branched alkyl or alkoxy group of about one to about ten carbons, said compound having at least one substituent.

Also provided in the present invention is a compound selected from the group consisting of 5,5'-dichloro-diindolylmethane; 5,5'-dibromo-diindolylmethane; 5,5'-difluoro-diindolylmethane; 5,5'-dimethyl-diindolylmethane; 5,5'-diethyl-diindolylmethane; 5,5'-dipropyl-diindolylmethane; 5,5'-dibutyl-diindolylmethane; 5,5'-dipentyl-diindolylmethane; 5,5'-dimethoxy-diindolylmethane; 5,5'-diethoxy-diindolylmethane; 5,5'-dipropyloxy-diindolylmethane; 5,5'-dibutyloxy-diindolylmethane; 5,5'-diamyloxy-diindolylmethane; N,N'-dimethyl-diindolylmethane; N,N'-diethyl-diindolylmethane; N,N'-dipropyl-diindolylmethane; N,N'-dibutyl-diindolylmethane; N,N'-dipentyl-diindolylmethane; 2,2'-dimethyl-diindolylmethane; 2,2'-diethyl-diindolylmethane; 2,2'-dipropyl-diindolylmethane; 2,2'-dibutyl-diindolylmethane and 2,2'-dipentyl-diindolylmethane.

A further object of the present invention is a pharmaceutical composition comprising a biologically active amount of a compound

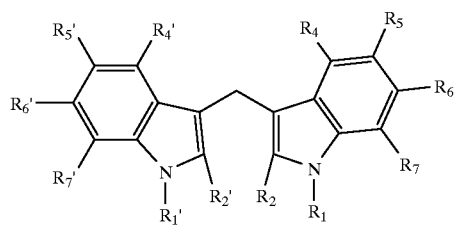

where $R_1$, $R_2$, $R_4$, $R_5$, $R_6$, $R_7$, $R_1'$, $R_2'$, $R_4'$, $R_5'$, $R_6'$, and $R_7'$, individually and independently, is a hydrogen, or a substituent selected from the group consisting of a halogen, a nitro group, and a linear or branched alkyl or alkoxy group of about one to about ten carbons, said compound having at least one substituent, and a pharmaceutically acceptable carrier.

An additional embodiment of the present invention is a method of treating estrogen-dependent tumors comprising administering a biologically active amount of a compound

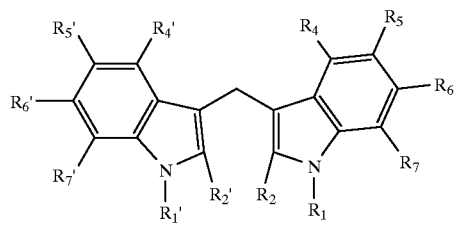

where $R_1$, $R_2$, $R_4$, $R_5$, $R_6$, $R_7$, $R_1'$, $R_2'$, $R_4'$, $R_5'$, $R_6'$, and $R_7'$, individually and independently, is a hydrogen, or a substituent selected from the group consisting of a halogen, a linear or branched alkyl or alkoxy group of about one to about ten carbons, and a nitro group said compound having at least one substituent.

DETAILED DESCRIPTION OF THE INVENTION

Provided in the present invention is a compound having the structure:

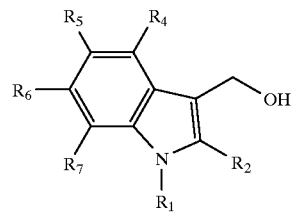

where $R_1$, $R_2$, $R_4$, $R_5$, $R_6$, and $R_7$ individually and independently, is a hydrogen, or a substituent selected from the group consisting of a halogen, a nitro group, and a linear or branched alkyl or alkoxy group of about one to about ten carbons, preferably of about one to about five carbons, said compound having at least one substituent. The halogen may be selected from the group consisting of chlorine, bromine and fluorine.

In a preferred embodiment of the I3C derivatives, $R_1$, $R_2$, $R_4$, $R_6$ and $R_7$ are hydrogen, and $R_5$ is a halogen selected from the group consisting of chlorine, bromine and fluorine. Accordingly, preferred I3C derivatives include 5-chloro-indole-3-carbinol, 5-bromo-indole-3-carbinol, and 5-fluoroindole-3-carbinol. Additional preferred I3C derivatives include compounds wherein $R_1$, $R_2$, $R_4$, $R_6$ and $R_7$ are hydrogen, and $R_5$ is an alkyl or alkoxyl having from one to ten carbons, and most preferably one to five carbons. These include, but are not limited to 5-methyl-indole-3-carbinol, 5-ethyl-indole-3-carbinol, 5-propyl-indole-3-carbinol, 5-butyl-indole-3-carbinol and 5-pentyl-indole-3-carbinol. These also include, but are not limited to, 5-methoxy-indole-3-carbinol, 5-ethoxy-indole-3-carbinol, 5-propyloxy-indole-3-carbinol, 5-butyloxy-indole-3-carbinol, and 5-amyloxy-indole-3-carbinol. Additional preferred I3C derivatives include compounds wherein $R_2$, $R_4$, $R_5$, $R_6$ and $R_7$ are hydrogen, and $R_1$ is an alkyl having from one to ten carbons, and most preferably one to five carbons. Such useful derivatives include, but are not limited to, N-methyl-indole-3-carbinol, N-ethyl-indole-3-carbinol, N-propyl-indole-3-carbinol, N-butyl-indole-3-carbinol, and N-pentyl-indole-3-carbinol. In yet another preferred embodiment, $R_1$, $R_4$, $R_5$, $R_6$ and $R_7$ are hydrogen, and $R_2$ is an alkyl of one to ten carbons, and most preferably one to five carbons. Such compounds include, but are not limited to, 2-methyl-indole-3-carbinol, 2-ethyl-indole-3-carbinol, 2-propyl-indole-3-carbinol, 2-butyl-indole-3-carbinol and 2-pentyl-indole-3-carbinol. In another embodiment, $R_1$, $R_2$, $R_4$, $R_6$ and $R_7$ are hydrogen, and $R_5$ is nitro.

Also provided herein is a compound having the structure:

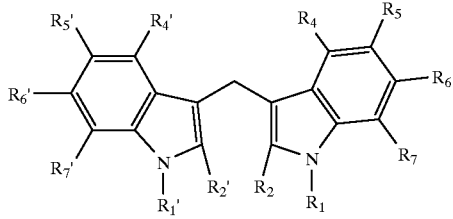

where $R_1$, $R_2$, $R_4$, $R_5$, $R_6$, $R_7$, $R_1'$, $R_2'$, $R_4'$, $R_5'$, $R_6'$, and $R_7'$, individually and independently, is a hydrogen, or a substituent selected from the group consisting of a halogen, a nitro group, and a linear or branched alkyl or alkoxy group of about one to about ten carbons, preferably of about one to about five carbons, said compound having at least one substituent. The halogen is selected from the group consisting of chlorine, bromine and fluorine. A compound such as this is referred to as a DIM derivative or a DIM analog.

In a preferred embodiment of the DIM derivatives, $R_1$, $R_2$, $R_4$, $R_6$, $R_7$, $R_1'$, $R_2'$, $R_4'$, $R_6'$, and $R_7'$ are hydrogen, $R_5$ and $R_5'$ are a halogen selected from the group consisting of chlorine, bromine and fluorine. Accordingly, preferred DIM derivatives include 5,5'-dichloro-diindolylmethane, 5,5'-dibromo-diindolylmethane, and 5,5'-difluoro-diindolylmethane. Additional preferred DIM derivatives include compounds wherein $R_1$, $R_2$, $R_4$, $R_6$, $R_7$, $R_1'$, $R_2'$, $R_4'$, $R_6'$, and $R_7'$ are hydrogen, $R_5$ and $R_5'$ are an alkyl or alkoxyl having from one to ten carbons, and most preferably one to five carbons. These include, but are not limited to 5,5'-dimethyl-diindolylmethane, 5,5'-diethyl-diindolylmethane, 5,5'-dipropyl-diindolylmethane, 5,5'-dibutyl-diindolylmethane and 5,5'-dipentyl-diindolylmethane. These also include, but are not limited to, 5,5'-dimethoxy-diindolylmethane, 5,5'-diethoxy-diindolylmethane, 5,5'-dipropyloxy-diindolylmethane, 5,5'-dibutyloxy-diindolylmethane, and 5,5'-diamyloxy-diindolylmethane. Additional preferred DIM derivatives include compounds wherein $R_2$, $R_4$, $R_5$, $R_6$, $R_7$, $R_2'$, $R_4'$, $R_5'$, $R_6'$, and $R_7'$ are hydrogen, $R_1$ and $R_1'$ are an alkyl or alkoxyl having from one to ten carbons, and most preferably one to five carbons. Such useful derivatives include, but are not limited to, N,N'-dimethyl-diindolylmethane, N,N'-diethyl-diindolylmethane, N,N'-dipropyl-diindolylmethane, N,N'-dibutyl-diindolylmethane, and N,N'-dipentyl-diindolylmethane. In yet another preferred embodiment, $R_1$, $R_4$, $R_5$, $R_6$, $R_7$, $R_1'$, $R_4'$, $R_5'$, $R_6'$, and $R_7'$ are hydrogen $R_2$ and $R_2'$ are alkyl of one to ten carbons, and most preferably one to five carbons. Such compounds include, but are not limited to, 2,2'-dimethyl-diindolylmethane, 2,2'-diethyl-diindolylmethane, 2,2'-dipropyl-diindolylmethane, 2,2'-dibutyl-diindolylmethane, and 2,2'-dipentyl-diindolylmethane. In another embodiment, $R_1$, $R_2$, $R_4$, $R_6$, $R_7$, $R_1'$, $R_2'$, $R_4'$, $R_6'$, and $R_7'$ are hydrogen, $R_5$ and $R_5'$ are nitro.

The synthesis of the substituted I3C derivatives from the commercially-available substituted indoles is probably the most convenient method for preparation of these compounds. The substituted DIM analogs can also be prepared by condensation of formaldehyde with substituted indoles; however, the disadvantage of the latter reaction is the formation of by-products which will complicate purification of the desired substituted DIM. The compounds of the present invention can be synthesized by dimethylformamide condensation of a suitable substituted indole to form a substituted indole-3-aldehyde. Suitable substituted indoles include indoles having substituents at $R_1$, $R_2$, $R_4$, $R_5$, $R_6$ and $R_7$ positions. These include, but are no limited to 5-methoxy, 5-chloro, 5-bromo, 5-fluoro, 5'-methyl, 5-nitro, n-methyl adn 2-methyl indoles. The substituted indole 3-aldehyde product is treated with a suitable alcohol such a methanol and solid sodium borohydride to reduce the aldehyde moiety to give substituted I3Cs. Substituted DIMs are prepared by condensing the substituted indole-3-carbinol products. This may be achieved, for example, by treatment with a phosphate buffer having a pH of around 5.5

Also provided is a pharmaceutical composition comprising a biologically active amount of a compound having the structure:

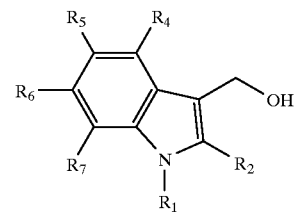

where $R_1$, $R_2$, $R_4$, $R_5$, $R_6$, and $R_7$ individually and independently, is a hydrogen, or a substituent selected from the group consisting of a halogen, a nitro group, and a linear or branched alkyl or alkoxy group of about one to about ten carbons, preferably of about one to about five carbons, said compound having at least one substituent. The halogen is selected from the group consisting of chlorine, bromine and fluorine.

It is also an object of the present invention to provide a method of treating estrogen-dependent tumors comprising administering a biologically active amount of a compound of the formula:

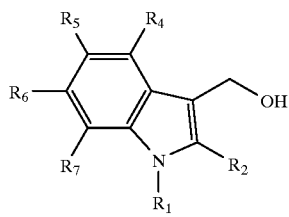

where $R_1$, $R_2$, $R_4$, $R_5$, $R_6$, and $R_7$, individually and independently, is a hydrogen, or a substituent selected from the group consisting of a halogen, a nitro group, a linear or branched alkyl or alkoxy group of about one to about ten carbons, preferably of about one to about five carbons, said compound having at least one substituent. The halogen is selected from the group consisting of chlorine, bromine and fluorine.

Also provided is a pharmaceutical composition comprising a biologically active amount of a compound having the structure:

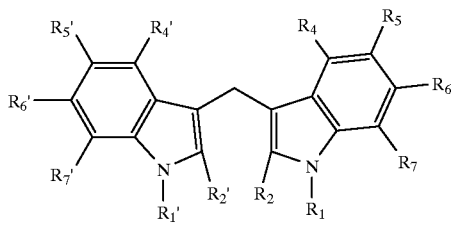

where $R_1$, $R_2$, $R_4$, $R_5$, $R_6$, $R_7$, $R_1'$, $R_2'$, $R_4'$, $R_5'$, $R_6'$, and $R_7'$, individually and independently, is a hydrogen, or a substituent selected from the group consisting of a halogen, a nitro group, and a linear or branched alkyl or alkoxy group of about one to about ten carbons, preferably of about one to about five carbons, and a nitro group said compound having at least one substituent. The halogen is selected from the group consisting of chlorine, bromine and fluorine.

A further embodiment of the present invention is method of treating estrogen-dependent tumors comprising administering a biologically active amount of a compound of the formula:

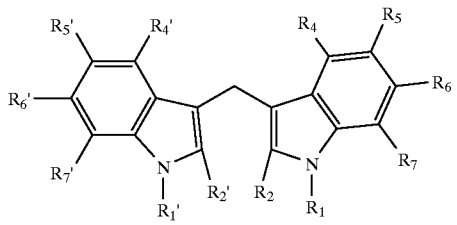

where $R_1$, $R_2$, $R_4$, $R_5$, $R_6$, $R_7$, $R_1'$, $R_2'$, $R_4'$, $R_5'$, $R_6'$, and $R_7'$, individually and independently, is a hydrogen, or a substituent selected from the group consisting of a halogen, a linear or branched alkyl or alkoxy group of about one to about ten carbons, preferably of about one to about five carbons, said compound having at least one substituent. The halogen is selected from the group consisting of chlorine, bromine and fluorine.

The agents of the present invention may be administered orally, intravenously, intranasally, rectally, or by any means which delivers an effective amount of the active agent to the tissue or site to be treated. Suitable dosages are those which achieve the desired endpoint. It will be appreciated that different dosages may be required for treating different disorders. An effective amount of an agent is that amount which causes a significant decrease in neoplastic cell count, growth, or size. Neoplastic disorders responsive to the agents of the present invention include, but are not limited to, breast cancer and endometrial cancer.

Those having ordinary skill in the art will be able to ascertain the most effective dose and times for administering the agents of the present invention, considering route of delivery, metabolism of the compound, and other pharmacokinetic parameters such as volume of distribution, clearance, age of the subject, etc.

The active agents may be administered along with a pharmaceutical carrier and/or diluent. The agents of the present invention may also be administered in combination with other agents, for example, in association with other chemotherapeutic or immunostimulating drugs or therapeutic agents. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to, corn oil, dimethylsulfoxide, gelatin capsules, etc.

The present invention is exemplified in terms of in vitro and in vivo activity against various neoplastic and normal cell lines. The test cell lines employed in the in vitro assays are well recognized and accepted as models for antitumor activity in animals. The term "animals" as used herein includes, but is not limited to, mice, rats, domesticated animals such as, but not limited to cats and dogs, and other animals such as, but not limited to cattle, sheep, pigs, horses, and primates such as, but not limited to monkeys and humans. The mouse experimental tumor in vivo assays are also well recognized and accepted as predictive of in vivo activity in other animals such as, but not limited to, humans.

The following examples serve to illustrate specific embodiments of the invention, but should not be considered as a limitation on the scope of the invention.

EXAMPLE 1

Preparation of Substituted Derivatives

The substituted indoles (e.g. 5-methoxy, 5-chloro, 5-bromo, 5-fluoro, 5-methyl 5-nitro, N-methyl and 2-methyl) are commercially available and the substitued indole-3-aldehydes (or carboxaldehyde) were prepared by condensation with dimethylformamide followed by hydrolysis of the dimethylamine. Dimethylformamide (2.9 ml) was cooled to 0° C. in an ice-salt bath and phosphorus oxychloride (0.86 ml) was added slowly over 30 min. The substituted indole (8.6 mmol) in 1.0 ml dimethylformamide was added slowly to the cooled solution over a period of 10 min and the resulting slurry was then heated at 35° C. for 60 to 90 min until the clear yellow solution became a yellowish paste. The thick slurry was added to 1 ml of water and ice, and 10 ml of aqueous potassium hydroxide solution (3.75 g KOH) was slowly added to reaction mixture (30 min) which was then heated to the boiling point and cooled in a refrigerator. The precipitated substituted indole-3-carboxaldehyde was filtered, washed with water, air-dried (yields~90%) and used for preparation of the I3C analogs.

The substituted indole-3-carboxyaldehydes (1.0 g) were dissolved in methanol (5 ml) and solid sodium borohydride was added over a period of 30 min and the reaction was continued until all the aldehyde was reduced as determined by thin-layer chromatography. The resulting solution was added to 50 ml of water, cooled to 0° C. and the substituted indole-3-carbinols collected by filtration and dried in a vacuum dessicator in the absence of light (yields 80 to 90%).

The substituted I3C analogs (1 g) were stirred at 20 to 25° C. for 6 to 12 hr in phosphate buffer (pH 5.5), and reaction Electronics, Hialeah, Fla.) as described by Liu et al., J. Natl. Cancer Inst., 86. 1758–1765, 1994; Tiwari et al., J. Natl, Cancer Inst. 86, 126–131, 1994. In some cases, 17-β-estradiol ($E_2$) ($1\times10^{-9}$ M) was also added in combination with the IC3 or DIM analogs.

TABLE 1

EFFECTS OF DIFFERENT CONCENTRATIONS OF I3C AND SUBSTITUTED ANALOGS ON THE GROWTH OF MCF-7 CELLS IN THE PRESENCE OF E2

| | | % of E2-Induced Response (Conc. of I3C Analogs) | | | | |
|---|---|---|---|---|---|---|
| Treatment | E2 (1 nM) alone | 0.1 μM | 1 μM | 10 μM | 50 μM | 100 μM |
| I3C + E2 | 100.00 ± 4.75 | 100.00 ± 5.70 | 96.27 ± 3.23 | 83.86 ± 2.46* | 36.85 ± 0.65* | 8.15 ± 1.00* |
| 5-Chloro-I3C + E2 | 100.00 ± 7.76 | 94.04 ± 11.22 | 92.38 ± 3.14 | 82.18 ± 4.55* | 29.83 ± 5.98* | 1.02 ± 0.22* |
| 5-Bromo-I3C + E2 | 100.00 ± 4.75 | 96.32 ± 6.97 | 97.34 ± 6.33 | 94.44 ± 2.47 | 59.65 ± 1.05* | 14.95 ± 0.72* |
| N-Methyl-I3C + E2 | 100.00 ± 7.27 | 95.64 ± 4.26 | 96.21 ± 1.66 | 47.76 ± 2.13* | 14.44 ± 0.90* | 3.91 ± 0.64* |
| 1,2-Dimethyl-I3C + E2 | 100.00 ± 7.42 | 97.96 ± 5.68 | 94.40 ± 7.73 | 65.90 ± 2.86* | 0.35 ± 0.24* | 0.42 ± 0.14* |
| 5-Methyl-I3C + E2 | 100.00 ± 7.42 | 87.82 ± 11.05 | 81.57 ± 10.84 | 53.03 ± 4.24* | 0.87 ± 0.11* | 0.57 ± 0.20* |
| 5-Methoxy-I3C + E2 | 100.00 ± 7.27 | 87.62 ± 5.40 | 78.39 ± 11.93 | 58.90 ± 7.96* | 2.97 ± 0.20* | 0.61 ± 0.14* |
| 5-Nitro-I3C + E2 | 100.00 ± 3.16 | 94.67 ± 2.05* | 92.71 ± 3.89* | 44.23 ± 3.34* | 1.71 ± 0.06* | 0.39 ± 0.06* |

*Significantly lower (p < 0.05) than cells treated with E2 alone.

TABLE 2

EFFECTS OF DIFFERENT CONCENTRATIONS OF DIM AND SUBSTITUTED ANALOGS ON THE GROWTH OF MCF-7 CELLS IN THE PRESENCE OF E2

| | | % of E2-Induced Response (Conc. of DIM Analogs) | | | | |
|---|---|---|---|---|---|---|
| Treatment | E2 (1 nM) alone | 0.01 μM | 0.1 μM | 1 μM | 5 μM | 10 μM |
| DIM + E2 | 100.00 ± 4.75 | 107.03 ± 8.43 | 97.34 ± 3.56* | 77.01 ± 5.16* | 22.52 ± 2.47* | 6.84 ± 0.71* |
| 5-Fluoro-DIM + E2 | 100.00 ± 3.16 | 90.26 ± 2.50 | 102.52 ± 2.63 | 77.13 ± 3.51* | 35.67 ± 5.13* | 8.46 ± 1.17* |
| 5-Chloro-DIM + E2 | 100.00 ± 7.76 | 98.39 ± 11.17 | 98.32 ± 8.34 | 87.26 ± 5.98 | 0.75 ± 0.10* | 0.99 ± 0.27* |
| 5-Bromo-DIM + E2 | 100.00 ± 3.16 | 99.03 ± 0.49 | 106.23 ± 3.38 | 75.01 ± 1.35* | 9.92 ± 0.58* | 0.30 ± 0.04* |
| N-Methyl-DIM + E2 | 100.00 ± 3.87 | 82.76 ± 10.77* | 96.38 ± 2.94 | 78.51 ± 3.03* | 3.92 ± 0.49* | 0.85 ± 0.12* |
| 5-Methoxy-DIM + E2 | 100.00 ± 3.87 | 87.22 ± 3.52* | 89.41 ± 3.12* | 69.44 ± 3.95* | 37.10 ± 4.52* | 11.36 ± 1.63* |

*Significantly lower (p < 0.05) than cells treated with E2 alone.

progress was monitored by TLC. The resulting substituted DIMs were filtered, dried in vacuo, and stored in the dark (yield 80 to 95%). These were confirmed by gas, liquid and thin-layer chromatography.

EXAMPLE 2

Effect of compounds on MCF-7 proliferation

This example demonstrates the effectiveness of the compounds of the present invention on MCF-7 human breast cancer cell growth. MCF-7 cells (50,000 per well) were grown in six-well plates in DME-F12 medium as described in Liu, et al., Mol. Cell Endocrinol, 87:19–28, 1992. The cells were given fresh medium plus the compounds being tested every other day. After 6 days of treatment, the cells were harvested and counted with a Coulter counter (Coulter These data in Tables 1 and 2 show that the compounds of the present invention inhibit the estrogen-induced growth of MCF-7 human breast cancer cells. This antiestrogenic activity shows these compounds will be useful in vivo for inhibiting mammary tumor growth.

EXAMPLE 3

Effect of Compounds on Tumor Volume

This example shows the effects of compounds on experimental tumor growth in vivo. Female virgin Sprague-Dawley rats were obtained from Harlan (Houston, Tex., U.S.A.) and were allowed to acclimate for 10 days, allowed access to food and water ad libitum, and maintained on a 12 h light/dark schedule. Mammary tumors were induced in 50±3 day old rats by administering a single gavage dose of 20 mg DMBA in 0.5 ml corn oil, as described. Huggins, C., et al.: Mammary cancer induced by a single feeding of polynuclearhydrocarbons and its suppression; Nature, 189, 204–207, 1961: Holcomb, M. and Safe, S.: *Cancer Letters,* 82, 43–47, 1994. After 30 to 75 days, tumors could be detected by palpation in the ductal tubes of the mammary glands. Multiple tumors often developed on a single rat; when the tumor or the largest of the tumors reached a small size (50 to 100 mm$^3$), the rats were treated with (a) corn oil alone (vehicle control) or methoxy-DIM at 5 mg/kg; and (b) corn oil or DIM at 5 mg/kg. Compounds were administered by intraperitoneal injection in corn oil (ml/kg). Each treatment group contained at least 10 animals which were treated every 2 days with the test chemical or vehicle control (corn oil). Tumor sizes were measured with calipers, and volumes were calculated by formula (length×width×depth)/6π.

TABLE 3

EFFECTS OF DIM AND DIM ANALOGS UPON TUMOR GROWTH AND TOXIC ENDPOINTS IN SPRAGUE-DAWLEY RATS IN THE DMBA-INDUCED MAMMARY CARCINOMA MODEL
A. 10 Treatments by gavage 5 mg/kg every other day, sacrificed day 21

| Treatment | N | Tumor Volume (% Control) | Tumor Weight (% Control) | EROD (% Control) | Liver Weight (% body weight) | Uterine Wet Weight (% body weight) |
|---|---|---|---|---|---|---|
| Control | 7 | 100.0 ± 26.0 | 100.0 ± 29.3 | 100.0 ± 23.1 | 4.07 ± 0.19 | 0.182 ± 0.016 |
| DIM | 7 | 19.9 ± 5.8** | 23.7 ± 6.0** | 106.1 ± 22.4 | 3.87 ± 0.22 | 0.184 ± 0.027 |
| 5-Methoxy-DIM | 6 | 22.1 ± 4.4** | 22.1 ± 4.4** | 151.2 ± 43.4 | 4.16 ± 0.23 | 0.224 ± 0.034 |
| 5-Fluoro-DIM | 6 | 35.8 ± 16.6** | 45.0 ± 20.0* | 157.6 ± 22.1 | 4.30 ± 0.29 | 0.208 ± 0.044 |

Values are expressed as mean ± standard error. Statistical analysis was determined using ANOVA and the Duncan New Multiple Range Test.
*Significant ≦ 0.05
**Significant ≦ 0.01

These results show that the substituted DIM derivatives are effective in vivo and inhibit growth of mammary tumors. The dose levels (5 mg/kg every 2 days) are relatively low compared to that of Tamoxifen in this same mode, showing that this group of AhR-based chemicals are an important new class of mammary tumor growth-inhibiting drugs.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method of treating estrogen-dependent tumors comprising administering a biologically active amount of a compound of the formula:

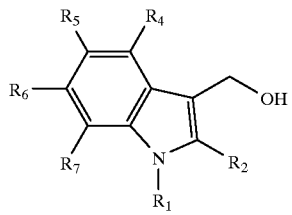

where $R_1$, $R_2$, $R_4$, $R_5$, $R_6$ and $R_7$, individually and independently, is a hydrogen, or a substituent selected from the group consisting of a halogen, a linear or branched alkyl or alkoxy group of one to ten carbons, and a nitro group, said compound having at least one substituent.

2. The method of claim 1 wherein said linear or branched alkyl or alkoxy group is one to five carbons.

3. The method of claim 1 wherein said halogen is selected from the group consisting of chlorine, bromine and fluorine.

4. The method of claim 1 wherein said compound is selected from the group consisting of 5-methyl-indole-3-carbinol, 5-ethyl-indole-3-carbinol, 5-propyl-indole-3-carbinol, 5-butyl-indole-3-carbinol, 5-pentyl-indole-3-carbinol, 5-methoxy-indole-3-carbinol, 5-ethoxy-indole-3-carbinol, 5-propyloxy-indole-3-carbinol, 5-butyloxy-indole-3-carbinol, 5-amyloxy-indole-3-carbinol, N-methyl-indole-3-carbinol, N-ethyl-indole-3-carbinol, N-propyl-indole-3-carbinol, N-butyl-indole-3-carbinol, N-pentyl-indole-3-carbinol, 2-methyl-indole-3-carbinol, 2-ethyl-indole-3-carbinol, 2-propyl-indole-3-carbinol, 2-butyl-indole-3-carbinol and 2-pentyl-indole-3-carbinol.

5. The method according to claim 1, wherein said estrogen dependent tumor is selected from the group consisting of breast cancer and endometrial cancer.

6. The method of claim 1 wherein the compound further comprises a pharmaceutically acceptable carrier.

7. The method of claim 6 wherein the pharmaceutically acceptable carrier is selected from the group consisting of corn oil, dimethylsulfoxide and gelatin capsule.

8. A method of treating estrogen-dependent tumors comprising administering a biologically active amount of a compound of the formula:

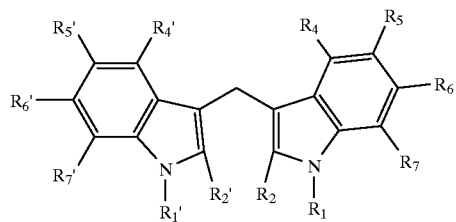

where $R_1$, $R_2$, $R_4$, $R_5$, $R_6$, $R_7$, $R_1'$, $R_2'$, $R_4'$, $R_5'$, $R_6'$ and $R_7'$ individually and independently, is a hydrogen, or a substituent selected from the group consisting of a halogen, a linear or branched alkyl or alkoxy group of one to ten carbons, and a nitro group, said compound having at least one substituent.

9. The method of claim 8 wherein said linear or branched alkyl or alkoxy group is one to five carbons.

10. The method of claim 8 wherein said halogen is selected from the group consisting of chlorine, bromine and fluorine.

11. The method of claim 8 wherein said compound is selected from the group consisting of 5,5'-dichlorodiindolylmethane; 5,5'-dibromo-diindolylmethane; 5,5'-difluoro-diindolylmethane; 5,5'-dimethyldiindolyl-methane; 5,5'-diethyl-diindolylmethane; 5,5'-dipropyl-diindolylmethane; 5,5'-dibutyl-diindolylmethane; 5,5'-dipentyl-diindolylmethane; 5,5'-dimethoxy-diindolylmethane; 5,5'-diethoxy-diindolylmethane; 5,5'-dipropyloxy-diindolylmethane; 5,5'-dibutyloxydiindolylmethane; 5,5'-diamyloxy-diindolylmethane; N,N'-dimethyldiindolyl-methane; N,N'-diethyldiindolylmethane; N,N'-dipropyl-diindolylmethane; N,N'-dibutyl-diindolylmethane; N,N'-dipentyl-diindolylmethane; 2,2'-dimethyl-diindolylmethane; 2,2'-dimethyldiindolyl-methane; 2,2'-dipropyldiindolylmethane; 2,2'-dibutyldiindolylmethane and 2,2'-dipentyl-diindolylmethane.

12. The method according to claim 8, wherein said estrogen dependent tumor is selected from the group consisting of breast cancer and endometrial cancer.

13. The method of claim 8 wherein the compound further comprises a pharmaceutically acceptable carrier.

14. The method of claim 13 wherein the pharmaceutically acceptable carrier is selected from the group consisting of corn oil, dimethylsulfoxide and gelatin capsule.

* * * * *